United States Patent [19]
Warren, III et al.

[11] Patent Number: 5,782,638
[45] Date of Patent: Jul. 21, 1998

[54] ORNAMENTAL FILM ARTICLE FOR DENTAL SUBSTRATE DECORATION AND DENTAL SUBSTRATE DECORATED THEREWITH

[76] Inventors: A. Daniel Warren, III, 4 Doctors Park; Gary E. Michels, 2245 Stantonsburg Rd. - Ste. F, both of Greenville, N.C. 27834; Steven J. Hultquist, P.O. Box 14329, Research Triangle Park, N.C. 27709

[21] Appl. No.: 596,042

[22] Filed: Feb. 6, 1996

Related U.S. Application Data

[63] Continuation-in-part of Ser. No. 445,363, May 19, 1995.
[51] Int. Cl.⁶ .................................................. A61C 5/08
[52] U.S. Cl. .................................. 433/206; 433/229
[58] Field of Search .............................. 433/206, 207, 433/215, 218, 219, 223, 229

[56] References Cited

U.S. PATENT DOCUMENTS

| | | | |
|---|---|---|---|
| 986,653 | 3/1911 | Supplee | 433/218 |
| 1,033,489 | 7/1912 | Tatham | 433/218 |
| 1,713,267 | 5/1929 | Crowley . | |
| 2,572,377 | 10/1951 | O'Morrow . | |
| 3,755,902 | 9/1973 | Northcutt | 433/4 |
| 3,760,502 | 9/1973 | Hirsch . | |
| 3,986,265 | 10/1976 | Cusato | 433/4 |
| 4,208,795 | 6/1980 | Muhlemann et al. . | |
| 4,439,154 | 3/1984 | Mayclin . | |
| 4,834,656 | 5/1989 | Loudon | 433/223 |
| 4,992,049 | 2/1991 | Weissman | 433/215 |
| 4,997,723 | 3/1991 | Tanaka . | |
| 5,104,320 | 4/1992 | Stoll | 433/206 |
| 5,110,290 | 5/1992 | Wong | 433/9 |
| 5,192,207 | 3/1993 | Rosellini | 433/223 |
| 5,256,064 | 10/1993 | Riihimaki et al. | 433/215 |
| 5,295,823 | 3/1994 | Farzin-Nia | 433/9 |
| 5,314,335 | 5/1994 | Fung | 433/218 |
| 5,320,532 | 6/1994 | Farzin-Nia et al. | 433/215 |
| 5,368,831 | 11/1994 | Tanaka . | |
| 5,509,805 | 4/1996 | Jagmin | 433/215 |
| 5,538,429 | 7/1996 | Mayclin | 433/218 |

FOREIGN PATENT DOCUMENTS

| | | | |
|---|---|---|---|
| 2624370 | 6/1989 | France | 433/206 |

*Primary Examiner*—Ralph Lewis
*Attorney, Agent, or Firm*—Steven J. Hultquist

[57] ABSTRACT

An ornamental metal foil appliqué for adhesive securement to a dental substrate, comprises a metal foil body having main top and bottom faces of a predetermined shape, preferably with a maximum facial area dimension not exceeding 1 centimeter. The main bottom face may be microetched over at least a major portion of its facial area to enhance the adhesive securement of the appliqué to the dental substrate and/or have a mesh backing member or other formaminous backing structure secured to such face of the metal foil body. The appliqué of the invention may be usefully employed for ornamenting a dental substrate of an individual whose mouth contains such dental substrate, by bonding the main bottom face of the shaped metal foil to the dental substrate with an adhesive medium so that the ornamental metal foil appliqué is in a selected display position on the dental substrate.

28 Claims, 10 Drawing Sheets

ORNAMENTAL FILM ARTICLE FOR DENTAL SUBSTRATE DECORATION AND DENTAL SUBSTRATE DECORATED THEREWITH

This application is a continuation-in-part of Ser. No. 08/445,363, filed 19 May 1995 and currently pending.

BACKGROUND OF THE INVENTION

1. Field of the Invention

The present invention relates to an ornamental appliqué article for decoration of a dental substrate, and to a dental substrate, e.g., a natural or artificial tooth, decoratively ornamented with such appliqué article, as well as to a method of making such appliqués and decorated substrates.

2. Description of the Related Art

In the field of apparel, jewelry, and bodily adornment, a number of decorative techniques have been utilized to impart an aesthetic and decorative appearance to the body.

In respect of teeth and other dental substrates, decorative efforts have been largely limited to tooth whiteners, capping and restoration techniques.

It would therefore be of interest to provide a novel adornment of teeth and other dental substrates, and it accordingly is an object of the present invention to provide same, comprising decorative means and decorative methodology which are readily utilized and economically applied.

In the prior art, U.S. Pat. No. 4,208,795 to H. R. Muhlemann, et al. describes the interior disposition in a tooth of an identifying member for forensic identification purposes. A shallow cavity first is drilled into the crown of a tooth, and an information carrier of durable material, such as a gold alloy plate bearing identifying information is inserted in the cavity. The cavity then is filled with a filling material which at least on its surface has a coloring which is visually identifiable, in contrast to the color of the dental crown surface, for location purposes.

U.S. Pat. No. 4,439,154 to P. J. Mayclin describes a similar technique, in which a carrier element with a Social Security number or other information thereon, is embedded in a slot prepared or cured just beneath the surface of a denture. The embedded element is covered with a clear material of the same type or compatible with the original material of the dental prosthesis.

U.S. Pat. No. 3,760,502 to A. J. Hirsch discloses the use of a thin veneer member of a planar configuration having an extremely thin width, substantially dimensionally congruent with a tooth. The veneer member has a relatively smooth front surface treated to provide a selected tooth coloration and a back surface featuring a fastening means. By such structure, the veneer may be used in conjunction with a crown, to afford coloring of the same, while permitting easy removal of the structure if discoloring or wear takes place, or if replacement is desired for any reason.

U.S. Pat. No. 1,713,267 to D. J. Crowley discloses an artificial tooth structure having inlaid identification characters, in which the identification characters are of dissimilar colors from each other and from the tooth structure, so that the characters may be more easily read, and so that different colors may define different classes of artificial teeth. The identification character may be formed of porcelain carrying a pigment or color, and may be inlaid as shown in FIG. 2 of the patent.

U.S. Pat. No. 2,572,377 to R. E. O'Morrow describes a backing used with interchangeable or replaceable artificial teeth or facings. The backing includes two permanently bonded layers of alloyed noble metals. One of the layers has a predominantly gold coloration and may be formed of a composition comprising gold in the amount of 47% to 75% by weight, silver from 18% to 45% by weight, and platinum from 1% to 8% by weight. The other layer is predominantly white in coloration, and is formed of a composition comprising gold in the amount of 20% to 30% by weight, silver in the amount of from 18% to 47% by weight, palladium in the amount of from 20% to 30% by weight, and platinum in the amount of from 0.5% to 8% by weight. In the use of such backing, the colors and hues of teeth of natural dentition are said to be acceptably matched by artificial teeth made of porcelain or plastic, regardless of whether the composition thereof is translucent or of a low translucence character.

U.S. Pat. No. 5,368,831 to A. Tanaka describes a ceramic inlay for filling cavities and teeth, comprising a layer of translucent ceramic material bonded to a metal foil layer. The metal foil layer can remain as part of the inlay or can be removed wholly or partially. The layer of foil is said to increase the strength of the inlay to a greater degree than would be expected on the basis of combining metal and ceramic. The patent discloses utilizing a foil layer which is so thin that it is invisible to the naked eye, thereby enhancing the aesthetic properties of the ceramic inlay. Foil layers of platinum, indium and gold are described. In the manufacture of the ceramic inlay, a foil is pressed and annealed into a desired shape, and disposed in a cavity of a mold. The ceramic then is built up on the foil by standard high temperature techniques (at temperatures for example of 900°–960° C., or other temperatures appropriate for ceramic material) resulting in a ceramic inlay bonded to the foil layer. The foil may be removed by grinding or peeling. When the foil is retained on the ceramic inlay, the foil is interiorly disposed in the restored tooth (see foil 12 on the ceramic layer 14 in FIG. 1). Thus, in contrast to the ornamental film article of the present invention, Tanaka does not contemplate a decorative appliqué on an exterior surface of a tooth or other dental substrate.

U.S. Pat. No. 5,104,320 issued Apr. 14, 1992 to Robert P. Stoll describes a precious metal tooth facing, comprising a dental veneer formed of a precious metal for attachment to the enamel surfaces of human teeth. The veneer comprises a generally preformed sheet-like body formed of precious metal and capable of being readily molded by the application of physical pressure to the tooth. The veneer includes an outer surface, a roughened concave inner surface, and knife edges between the outward and inward surfaces to provide a smooth, ledgeless transition between the facing and the enamel of the tooth to which it is bonded. Bonding may be by means of bonding agents suitable for use with precious metals.

It is an object of the present invention to provide an ornamental film article as an appliqué for decoration of a dental substrate, for aesthetic enhancement thereof.

It is another object of the present invention to provide an appliqué of such type, for forensic or other identification purposes.

It is yet a further object of the invention to provide an appliqué for a prosthetic tooth.

It is yet another object of the invention to provide a method of ornamenting a dental substrate, by means of which a decorative artifact can be applied to a tooth surface for a predetermined period of time, and subsequently readily removed.

Other objects and advantages of the invention will be more fully apparent from the ensuing disclosure and appended claims.

SUMMARY OF THE INVENTION

The present invention relates in one aspect to an ornamental metal foil appliqué for adhesive securement to a dental substrate.

The appliqué comprises a metal foil body having main top and bottom faces of a predetermined shape and size, preferably with a maximum facial area dimension preferably not exceeding 1 centimeter, although the specific size of the appliqué may be selectively varied in the broad practice of the present invention, depending on the specific size, shape, and available area (for affixation of the appliqué) of the dental substrate.

The appliqué in one aspect of the invention may be secured on the main bottom face of the metal foil body to a foraminous backing structure such as a grid, mesh, screen, or gauze, formed of a rigid material such as metal, ceramic, polymer, etc., with a metal wire mesh being preferred, of a material of construction such as stainless steel or gold. The foraminous backing structure may be secured to the main bottom face of the appliqués foil body by any suitable means and method of securement, such as brazing, welding, adhesive bonding, etc., with initial tack welding following by brazing being a preferred securement method of coupling the backing structure with the metal foil body of the appliqué.

It will be recognized that the terms "top" and "bottom" in reference to the faces of the metal foil body are for ease of reference only, in respect of a metal foil structure (sheet) in lay-flat position as reposed on a generally flat supportive surface. Such metal foil body as ultimately mounted on a vertically upstanding dental substrate such as a tooth, would have the "bottom" face in facing relationship to the dental substrate surface and the "top" face in outwardly facing relationship to the substrate. Accordingly, in such orientation, the bottom main face of the metal foil body would be the rear face and the top main face of the metal foil body would be the front face.

As used herein, the term "maximum facial area dimension" means the longest distance across the surface of the appliqué as applied to the dental substrate, as measured from edge to edge of the appliqué.

The main bottom face of the appliqué may optionally be lightly microetched over at least a major portion of its facial area, to enhance the capability of the foraminous backing structure to be secured to the foil body, such as by means of an adhesive, brazing, welding, etc., but in the broad practice of the invention, it generally is not necessary to perform such microetching or other surface enhancement of the metal foil's body which is to be joined to the foraminous backing structure. The main top face of the metal foil body is non-microetched over its facial area.

The metal foil body of the ornamental metal foil appliqué may have any suitable shape, size and edge surface conformation, but the metal foil body is desirably beveled at its margins for conformity at its edges with the dental substrate. The metal foil body of the ornamental metal foil appliqué may be formed of any appropriate metal, such as a metal selected from the group consisting of copper, brass, bronze, platinum, palladium, gold, silver, indium, iridium, palladium, rheuthenium, chromium, stainless steel, aluminum, titanium, and alloys, mixtures, and composites thereof. The metal foil body may for example comprise a gold alloy of a type commonly utilized in the dental and orthodontic arts or otherwise for intraoral use.

Dimensionally, the ornamental metal foil appliqué of the invention may utilize a metal foil body having a thickness in the range of from about 0.02 millimeter to about 0.5 millimeter, and more preferably from about 0.05 millimeter to about 0.16 millimeter, with a maximum facial area dimension not exceeding about 0.75 centimeter, and preferably not exceeding about 0.6 centimeter. Where a foraminous backing structure is employed, comprising a wire mesh member, the wire strands of the mesh may for example be on the order of about 0.025 to about 0.010 inch and the mesh size of the wire mesh member may be on the order of from about 50 to about 120.

In a specific embodiment, including a foraminous backing structure in the form of a stainless steel mesh, the ornamental metal foil appliqué may comprise a gold foil of 0.010 inch thickness, and a mesh backing including wires of 0.004–0.005 inch diameter, with a mesh size 80 grid of wires, having a spacing of 0.007 between the wires, although 60–100 mesh size backing structures may variously be employed. The mesh backing structure is tack welded to the foil and then brazed on the foil. Thus, the total thickness of the appliqué is on the order of 0.013 to 0.014 inch. The gold foil is made of a dental alloy commercially available and commonly applied to intraoral use.

In another aspect, the present invention relates to an ornamented dental article, comprising a dental substrate, and an ornamental metal foil appliqué in accordance with the invention, adhesively secured to a dental substrate.

As used herein, the term "dental substrate" means a natural or artificial tooth or teeth structure resident in use in the oral cavity of an animal, e.g., a mammal such as a human or non-human mammal (dog, horse, cow, etc.), and thus comprises natural teeth, as well as artificial dentures as well as caps, crowns, bridges and other restorations.

Further, the terms "ornamental" and "ornamenting" as used herein are intended to be broadly construed to encompass decorative and aesthetic enhancement usages of the appliqué of the invention, as well as identification or advertising usages of such appliqués. By way of example, the appliqué of the invention may be utilized for livestock and pet identification purposes, providing a marking which is less time-consuming and simpler to apply, less susceptible to willful obliteration or alteration, and less painful to the livestock than conventional branding. Additionally, the appliqué could be used in the case of application to human teeth for forensic identification.

In another aspect, the invention relates to a method of ornamenting a dental substrate, comprising the steps of:
providing an ornamental metal foil appliqué, comprising a metal foil body with main top and bottom surfaces, having a predetermined shape and of suitable size, preferably with a maximum facial area dimension not exceeding 1 centimeter;
optionally (I) securing a foraminous backing structure to the main bottom face of the shaped metal foil, or alternatively (II) microetching the main bottom face of the shaped metal foil over at least a major portion of its facial area; and
bonding the main bottom face of the shaped metal foil to the dental substrate with an adhesive medium.

In a preferred practice of the invention, the ornamentation afforded by the appliqué is reversible, with the metal foil appliqué and the adhesive medium being selected so that the metal foil appliqué when bonded to the dental substrate is abrasively removable from the dental substrate by dental abrasion. Alternatively, the appliqué could be secured to the dental substrate so that removal of the appliqué can be readily effected by the use of solvents, debonding agents, or thermal debonding. Thermal debonding may allow the removal of the appliqué by softening of the bonding agent, or alternatively by employing differential thermal expansion or contraction to effect detachment of the secured metal foil from the dental substrate to which the foil has been adhesively secured.

The method of the invention may be carried out with suitable preparation of the foil film for effecting adhesive attachment of the foil film to the tooth or other dental substrate surface.

Such preparation of the foil film may for example comprise microetching the main bottom surface of the metal foil body prior to adhesively bonding same to the dental substrate. The microetching advantageously comprises directing an abrasive medium at the surface to be bonded, at sufficient rate and flux to microetch such surface. Alternatively, other microetching techniques could be used, including etching by means of chemical etchants, radiation impingement on the surface to be bonded, etc. When an abrasive medium is utilized for impacting on the surface to be bonded, the abrasive medium may comprise a particulate material such as for example alumina, silica, and zirconia powders, having suitable particle size characteristics for the desired microetching operation.

Alternatively, the appliqué metal foil may bonded or otherwise secured to a backing member, such as the aforementioned foraminous backing structure or other structural element or member which is interposed between the metal foil bottom or rear surface and the surface of the dental substrate to be appliquéd with the ornamental appliqué article of the invention. The backing member may comprise an adhesive or sealant layer or may comprise a structure which is more readily bonded or secured to the dental substrate surface than the metal foil body itself.

When the backing member comprises a foraminous backing structure, the structure preferably comprises a mesh structure including interwoven strands in the form of an array of spaced-apart horizontal strands and an array of spaced-apart vertical strands wherein the respective strand arrays are disposed at right angles to one another. The mesh structure suitably is formed of a metal, although any suitable material of construction may be employed which is compatible with the other elements in the appliqué. A preferred metal is stainless steel.

As a still further alternative, the appliqué metal foil may have deposited thereon by sputtering, chemical vapor deposition, physical vapor deposition, electroless or electrolytic deposition, metal spray, solution evaporation, or any other suitable technique, a same or different metal (relative to the metal constituent(s) of the foil) which is discontinuously deposited on the appliqué metal foil on the rear surface thereof (the surface which when the appliqué metal foil is secured to the tooth, will be facing the tooth surface), so as to provide a textured surface of the applied discontinuous metal on such rear surface of the metal foil.

Such rear surface of the metal foil will therefore have surface asperities formed by the deposited metal, providing involutions and/or discontinuities in the applied metal which enhance the bondability of the appliqué metal foil to the dental substrate. In such manner, a "virtual mesh" structure is provided by the discontinuous metal applied to the back of the metal foil, by means of which the appliqué is readily adhesively bondable to the dental substrate.

In a still further method aspect, the present invention relates to a method of ornamenting a dental substrate of an individual whose mouth contains said dental substrate, comprising the steps of:

providing an ornamental metal foil appliqué, comprising a metal foil body with main top and bottom surfaces, having a predetermined shape and of suitable size, preferably with a maximum facial dimension not exceeding 1 centimeter;

optionally (I) securing a foraminous backing structure to the main bottom face of the shaped metal foil, or alternatively (II) microetching the main bottom face of the shaped metal foil over at least a major portion of its facial area;

bonding the main bottom face of the shaped metal foil to the dental substrate (through the intermediate foraminous backing structure if such is provided) with an adhesive medium so that the ornamental metal foil appliqué is in a selected display position on the dental substrate;

displaying the ornamental metal foil appliqué on the dental substrate in the individual's mouth for a predetermined period of time; and at the conclusion of said predetermined period of time, removing the ornamental metal foil appliqué from the dental substrate.

The ornamental metal foil appliqué may be removed from the dental substrate, if desired, by any suitable method and with any suitable means appropriate therefor.

In some instances, particularly where the metal foil appliqué is intended to be used only briefly or temporarily as a dental substrate ornamentation, the appliqué may be provided on its rear face with a low tack adhesive of appropriate type, so that the appliqué is manually readily removable by the wearer, without the aid of tools or instruments.

Alternatively, the appliqué may be adhesively or otherwise affixed in the first instance to the dental substrate, so as to be readily removable by the wearer with a suitable tool or instrument, such as a stylus or pick.

As yet another alternative, which may be utilized when the appliqué is bonded with a dental bonding cement or adhesive, so as to provide a significant usage life on the dental substrate, the appliqué may advantageously be removed from the dental substrate by dental abrasion. As used herein, the term "dental abrasion" means a level of abrasion typically used in the practice of dentistry for the removal of tooth structure, metal, or composite resin restorative materials.

In the use of the appliqué of the present invention, the metal foil body may be formed into any appropriate shape for the desired application, e.g., in a shape selected from the group consisting of silhouettes, initials, geometrically regular shapes, astrological signs, words, alphanumerics, numerics, and fanciful designs.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
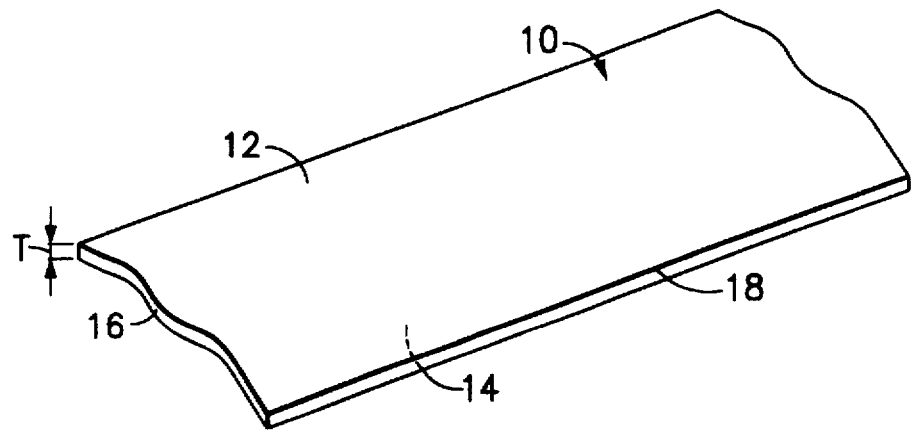
FIG. 1 is a perspective view of a metal foil strip useful as a precursor for the decorative appliqué of the present invention, in one embodiment thereof.

Referring now to the drawings, FIG. 1 is a perspective view of a metal foil strip 10 useful as a precursor for the decorative appliqué of the present invention.

The metal foil strip 10 has a thickness T which may for example be on the order of from about 0.02 to about 0.5 millimeter, and more particularly from about 0.05 millimeter to about 0.16 millimeter, although any other suitable thicknesses can be employed in the broad practice of the invention. The reasons for the specific thickness ranges are that the metal foil should not be so thin as to be susceptible to damage in use of the dental substrate, and the metal foil on the other hand should not be so thick as to be uncomfortable in defining a raised surface extending upwardly from the dental substrate surface to which the metal foil is affixed. The aforementioned broad, and progressively narrower, ranges of metal foil thickness represent balances between these competing considerations.

The metal foil strip 10 has a main top surface 12 and a main bottom surface 14 defining the thickness T therebetween, and bounded by the front edge 18 and side edge 16 in the view shown.

The metal foil strip may be formed of any suitable metal, as for example copper, brass, bronze, platinum, palladium, indium, gold, silver, iridium, rheuthenium, chromium, stainless steel, aluminum, titanium, and alloys, mixtures, and composites thereof. Preferably, the metal foil body comprises a noble or high noble metal, and most preferably the metal foil body comprises a gold foil, due to the superior ductility, non-corrosive, biocompatible, hypoallergenic and decorative characteristics thereof.

Figure 2:
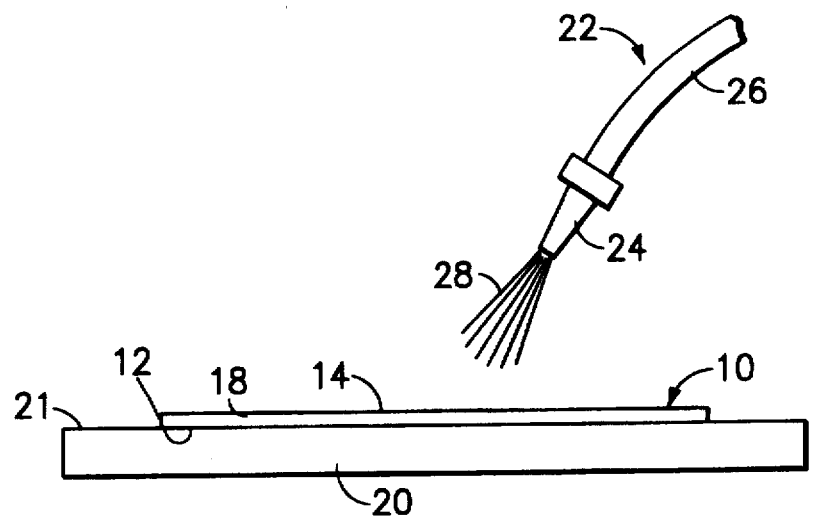
FIG. 2 is a front edge elevation view of the metal foil strip of FIG. 1 being mechanically abraded by impingement thereon of a particulate abrading material.

FIG. 2 is a front edge elevation view of the metal foil strip 10 of FIG. 1 being mechanically abraded, by impingement thereon of a particulate abrading material.

In FIG. 2, the metal foil strip 10 is shown in invertedly positioned relationship to that shown in FIG. 1, with the metal foil strip in FIG. 2 being reposed on its main top surface 12 against the top surface 21 of platen member 20, with the front edge 18 of the metal foil strip being displayed in the view shown. The main bottom surface 14 of the metal foil strip 10 thus is presented to the sand blaster-type abrader 22, comprising nozzle 24 coupled with delivery hose 26 which in turn is joined to a suitable source of particulate abrasive material and compressed gas (from sources not shown in FIG. 2). The hose 26 may for example be coupled to an air compressor delivering compressed air, into which is entrained a fine particulate material, such as a powder of alumina, silica, or zirconia, having a particle size in the range for example of from about 20 to about 150 micrometers.

There is resultingly produced a jet 28 of abrasive particles in the carrier gas which is directed at suitably high velocity at the main bottom surface 14 of the foil strip 10, as shown in FIG. 2. Microetching of the main bottom surface is thereby effected, so that decorative appliqué subsequently formed from such metal foil strip has a roughened, microetched surface. Such microetched surface facilitates adhesive bonding thereof to the dental substrate, as described hereinafter in greater detail.

While the metal foil may as illustrated in FIG. 2 be mechanically abraded by impingement thereon of abrasive powders or particles, other means and methods of etching or abrading the surface may be usefully employed in the broad practice of the present invention, whereby the surface is mechanically altered or chemically etched to increase its roughness and localized surface asperities, to enhance the adhesion of the resulting microetched film to the dental substrate.

It therefore will be appreciated that the metal foil may be etched or subjected to other appropriate surface preparation, to facilitate subsequent affixation of the metal foil appliqué to the dental substrate, in any suitable manner and with any suitable surface preparation means for such purpose, e.g., via chemical etchants, pulsed laser etching, ion beam bombardment of the metal foil surface, etc. It will also be appreciated that such surface preparation of the metal foil may be carried out at any time prior to the affixation of the appliqué to the dental substrate, e.g., before or after the appliqué is cut from the precursor sheet of metal foil.

For the purpose of mechanically abrading the surface of the metal foil which is subsequently to be bonded to the dental substrate, by microetching thereof, a Microetcher™ Model ERC Precision Sandblaster (Danville Engineering, Inc., Danville, Va.) may be usefully employed. Such unit comprises a micro-sandblasting hand piece, a 9 foot airline, and an abrasive reservoir secured and actuated in the resulting assembly by a finger button control valve. A suitable commercially available powder for use with such microetching apparatus is 50 micron aluminum oxide (Danville Engineering, Inc., Danville, Va.).

As an alternative to the use of the aforementioned sandblaster-type microetcher apparatus, a compatible chemical etchant may be usefully employed for the preparation of the main bottom surface of the metal foil strip, to enhance its adhesive bondability. Any known chemical etchant which is etchingly effective for the metal foil may be employed, including acid materials such as sulfuric, nitric, hydrochloric, and hydrofluoric acids, the choice of a specific etchant dependent on the specific metal, its film thickness, and its affinity for the specific adhesive medium employed.

Correspondingly, other etchant materials may also be employed to etch the tooth or dental substrate surface to which the metal foil is to be bonded, to enhance the adhesive bond strength afforded by the dental substrate surface. For such purpose, conventional etchants utilized in dentistry for etching preparation of the tooth surface to enhance the bondability of same, may be used to enhance the adhesive bonding of the appliqué to the dental substrate. Examples of such teeth etchant materials include Etchant-Light Green (Reliance Orthodontic Products, Itasca, Ill.), a chemical etchant which is conventionally employed to etch tooth surfaces in preparation for bonding of the tooth, e.g., to a cap, crown, or other dental restoration structure.

As discussed, the surface preparation of the metal foil bonding surface for subsequent affixation of the appliqué may be carried out at any suitable point in the appliqué fabrication process, e.g., a step of etching or abrading the surface of the metal foil may be carried out before or after the appliqué is cut out of a sheet of metal.

Figure 3A:
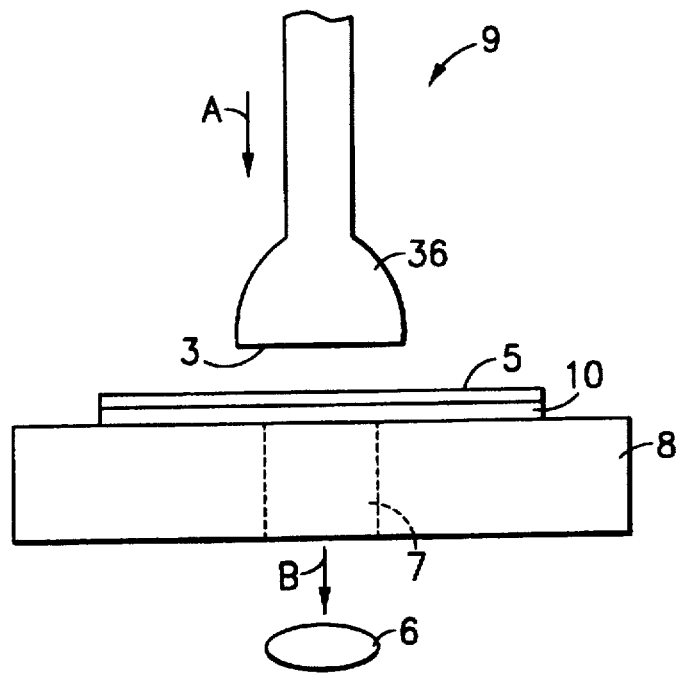
FIG. 3A is a front elevation view of a stamping apparatus assembly for forming a "blank" for the appliqué from the metal foil of FIG. 2, according to one embodiment of the invention.

FIG. 3A is a front elevation view of a stamping apparatus assembly 9 for forming a "blank" 6 for the appliqué from the metal foil strip 10 of FIG. 2, according to one embodiment of the invention. As shown, the metal foil strip 10 is disposed on a substrate 8 having a forming passage 7 therein, in the form of a cylindrical bore, as shown.

The metal foil strip 10 is overlaid with a plastic laminate film 5 of suitable material and thickness. The purpose of the plastic laminate film 5 is to protect the top surface of the metal foil strip so that the resulting appliqué is not scratched or otherwise damaged during the forming process.

To form the appliqué from the metal foil strip as shown in FIG. 3A, the stamping die 36 having a bottom flat stamping face 3 is downwardly translated in the direction indicated by arrow A in FIG. 3A, to resultingly cut from the metal foil film the planchet 6. The planchet 6 as illustrated is discharged from the passage 7 of substrate 8 in the direction indicated by arrow B. Various other stamping, punching, cutting, or etching processes may be employed within the broad practice of the present invention to form the appliqué element from the metal foil precursor therefor. Examples of such alternative formation processes include water jet cut out and wire EDM techniques, as well as chemical vapor deposition, in which the appliqué element is directly formed in the desired shape on a masked substrate by thin film deposition techniques of known and conventional character.

Figure 3B:
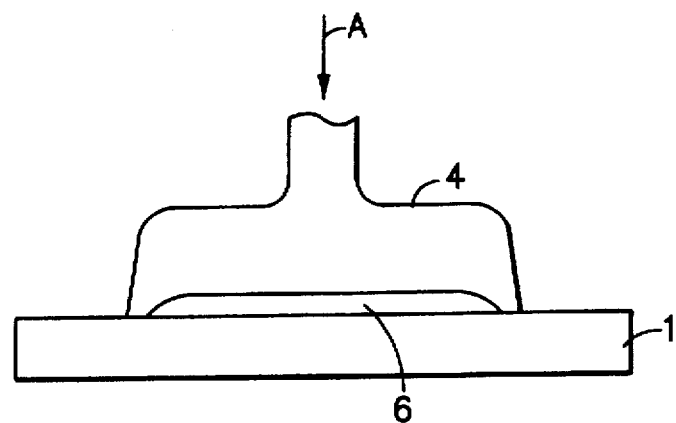
FIG. 3B is a front elevation view of an edge forming apparatus being employed to contour the edges of the "blank" of the appliqué formed by the apparatus of FIG. 3A.

FIG. 3B is a front elevation view of an edge forming apparatus being employed to contour the edges of the "blank" or planchet 6 formed by the apparatus of FIG. 3A. In FIG. 3B, the blank 6 is shown reposed on the substrate 1, with a forming die 4 being translated in the direction indicated by arrow A into forming contact with the blank, to bevel, "coin," or otherwise contour the edges of the blank. In the event that the blank 6 is to be used in uncontoured form, the step illustrated in FIG. 3B may be eliminated from the processing sequence for making the appliqué.

Figure 3C:
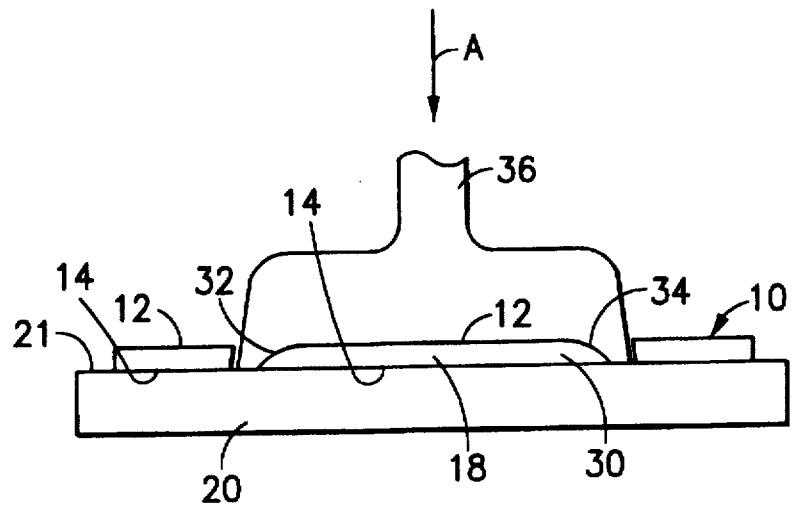
FIG. 3C is a front edge elevation view of the metal foil of FIG. 2, in contact with a forming die and platen, and forming the metal foil main body portion of the appliqué.

FIG. 3C is a front edge elevation view of the metal foil strip 10 of FIG. 2, in contact with a forming die 36 and platen 20, and forming the metal foil main body portion 30 of the appliqué 60.

The metal foil strip 10 as shown is reposed with the main bottom surface 14 in contact with the main top surface 21 of the platen 20. A forming dye 36 is downwardly directed (in the direction indicated by arrow A in FIG. 3), to form the main body portion 30 of the appliqué from the metal foil strip 10. The cutting edge surfaces of the interior cavity of the dye are curved as shown in FIG. 3, in consequence of which the main body portion 30 of the appliqué is formed with beveled or curvate edges 32 and 34. Alternatively, a two step process can be used wherein the appliqué is cut out in the first step and the edge beveled in a second step. The appliqué may as mentioned hereinabove be alternatively formed via water jet cut out or wire EDM techniques.

Still referring to FIG. 3, a transparent laminate 62 is optionally disposed on main top surface 12 of metal foil strip 10 to avoid ruining a highly polished main top surface 12 during manufacture of the appliqué. The protective laminate is removed after manufacturing or application of the appliqué to the dental substrate.

Figure 4:
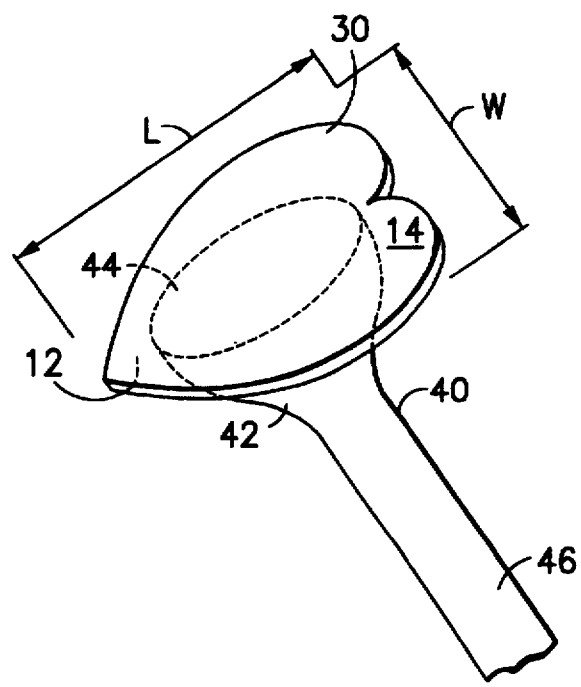
FIG. 4 is a perspective view of the metal foil main body portion of FIG. 3, mounted on an applicator device, and having the bottom surface thereof receiving an applied adhesive, for subsequent bonding of the appliqué to the surface of a tooth.

The cavity and cutting surfaces of the dye 36 may be formed with any suitable shape commensurate with the shape of the appliqué to be cut from the metal foil strip, such as the heart-shaped appliqué 60 shown in FIG. 4.

FIG. 4 is a perspective view of the metal foil main body portion 30 of FIG. 3, mounted on an applicator device 40, and having the bottom surface 14 thereof bearing an applied adhesive 31, for subsequent bonding of the appliqué 60 to the surface of a tooth.

The metal foil main body portion 30 of the appliqué 60 is shown with its main top surface affixed, as for example by a suitable low-tack adhesive or suction cup to the face 44 of applicator 40, which comprises a stem 46 and a flared distal portion 42 terminating in face 44.

Alternatively, a transparent "Scotch™" tape-like backing material can be used to apply the appliqué to the tooth, whereby the main top surface of the appliqué is attached to the tape-like material. The main bottom surface of the appliqué has a suitable adhesive applied thereon, as for example by transfer of adhesive thereto from an appropriate applicator or adhesive dispenser. In use, the edges of the tape-like backing material are held by an individual desiring to apply the appliqué to a dental substrate. The appliqué then is transferred from the tape-like backing material to the surface of a dental substrate by positioning and securing the bottom main surface of the appliqué on the substrate and peeling the tape-like material away.

The adhesive 31 on the main bottom face 14 of the appliqué may alternatively be applied by brushing, roller coating, or in any other suitable manner by which the adhesive is suitably coated on the main bottom surface 14 to ensure its appropriate bonding to the dental substrate. The adhesive 31 may be applied as a continuous film or coating, or it may alternatively be applied in a pattern or to selected areal portions of the facial surface (of the main bottom surface) of the appliqué.

The adhesive used to bond the appliqué to the dental substrate may comprise any suitable bonding medium and includes both light and self-curing adhesives. Examples include Transbond Light Cure Orthodontic Adhesive system with primer (3M Unitek Corporation, Monrovia, Calif.), or a self curing system such as Phase II (Reliance Orthodontic Products, Itasca, Ill.), Amlgabond or All Bond. The adhesive material may be of any suitable curable type, including light-cure (photopolymerizable) and auto-cure (anaerobic or otherwise reactively curing) materials. Methacrylate-based adhesives, e.g., comprising a curable resin component such as methyl methacrylate, are usefully employed in the broad practice of the invention, due to the widespread commercial use of such adhesives in dental applications, for adhesion of restorations, orthodontic brackets, etc.

As shown in FIG. 4, the heart-shaped appliqué 60 comprising the correspondingly shaped main body portion 30 has a length L defining the maximum facial area dimension of the appliqué. Also shown is the lateral width direction W of such facial area. As used herein, the term "facial area" refers to the surface area of the face of the appliqué, so that for example an appliqué of square shape with a side dimension, S, would have a facial area of $S^2$.

The maximum facial area dimension of appliqués in the practice of the present invention (which in the illustrative square shape example would be the length of the diagonal of the square, viz., 1.414 x S), in application to human teeth or other dental substrate employed in the oral cavity of a human or other mammalian subject, preferably should not exceed about 1 centimeter, more preferably not exceeding about 0.75 square centimeter, and most preferably not exceeding about 0.6 square centimeter, in order to provide a size appropriate to the dental substrate to which the appliqué is applied, while at the same time having sufficient size to ensure ready visibility of the appliqué on the dental substrate.

Since dental substrates can be of significantly differing sizes, the appliqué may be of correspondingly varying size characteristics. For example, a fairly large appliqué may be on the order of 8 millimeters in height or width (or other linear distance or dimension serving as a measure of the size of the main top surface of the appliqué).

While the preceding discussion herein has been directed to an appliqué article having a selected shape, as cut, punched or otherwise formed from a metal foil, it will be appreciated that the appliqué of the invention may be formed from a foil article of appropriate dimensional characteristics, as a metal foil "blank" in which a shape or portion is removed to provide a silhouette, or cut-out outline of the desired design or shape. In this manner, the appliqué may for example comprise a rectangular or square shaped blank, in which the design or shape, e.g., a star shape is cut out, so that the tooth (dental substrate) surface "shows through" the surrounding border of the appliqué. Further, the cut out may be in a number of various constituent cut out portions, to thereby form a picture or design of desired character.

It will be recognized in respect of the foregoing discussion that while the dental substrate may vary in size, the preferred size ranges set out hereinabove for the appliqué are defined so that the appliqué has an appropriately decorative character in relation to the surface of the dental substrate to which the appliqué is applied, i.e., is of a visually distinctive character.

The area of each of the main top and bottom faces of the appliqué thus constitutes the facial area of such face, and has a maximum facial dimension which is dimensionally measured on the face of the appliqué between the edges of maximum opposite separation distance, across the surface of the appliqué. For a circular appliqué, the maximum facial area dimension therefore will be the diameter D corresponding to the facial area $\pi \times (D/2)^2$, and for a quadrilateral regular shaped appliqué, the maximum facial dimension will be the length of the diagonal between diagonally opposite apices of such shaped appliqué.

Relative to the applicator-mounted appliqué 60 shown in FIG. 4, it is to be recognized that the adhesive 31 on the main bottom surface 14 of the appliqué is of a highly adhesive character, in relation to the low-tack adhesive material securing the opposite (main top) face 12 of the appliqué to the face 44 of the applicator, so that upon contact of adhesive-bearing main bottom face 14 with the dental substrate, the appliqué 60 is readily disengaged from face 44 of the applicator.

Instead of a low-tack adhesive on face 44 of the applicator, the applicator may be constructed to provide appropriate suction or other securement of the appliqué thereto, to facilitate the translation of the appliqué to the tooth and positioning of the appliqué on the tooth. Alternatively, other applicator devices or methods may be advantageously employed.

Figure 5A:
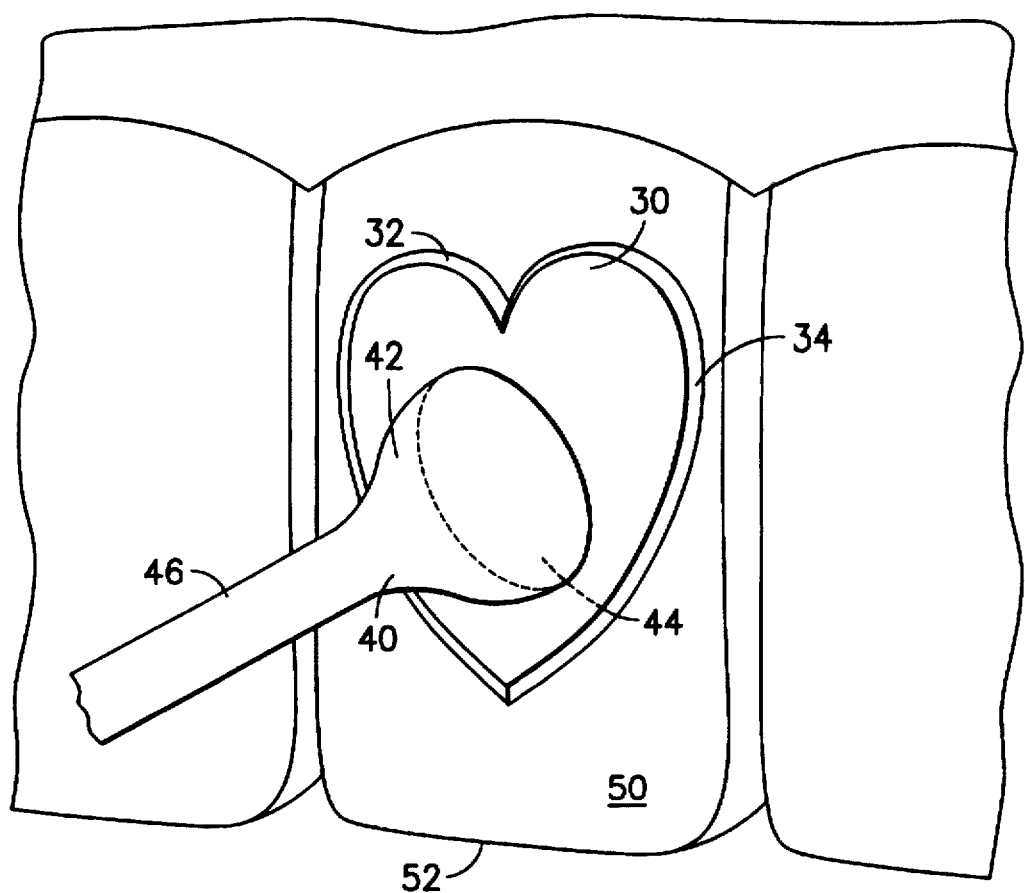
FIG. 5A is a perspective view of the appliqué of FIG. 4 being applied to the tooth surface of a wearer.

FIG. 5A is a perspective view of the appliqué 60 of FIG. 4 being applied to the tooth surface 50 of a wearer.

As illustrated, the appliqué 60 is translated by applicator 40 so that the main body portion 30 of the appliqué is in contact with the surface 50 of tooth 52, with the adhesive on the main bottom face of the appliqué in direct bearing contact with the tooth surface. In such manner, pressure may be applied manually on the stem 46 of applicator 40, to cause corresponding compressive force to be exerted through face 44 to the main body portion 30 of appliqué 60, and so that the bonding medium on the appliqué rear surface appropriately bonds to the surface 50 of tooth 52.

Once bonding has been effected, the applicator 40 may be withdrawn from the main top surface 12 of the appliqué, so that the appliqué thereafter is in bonded position on the tooth.

Figure 5B:
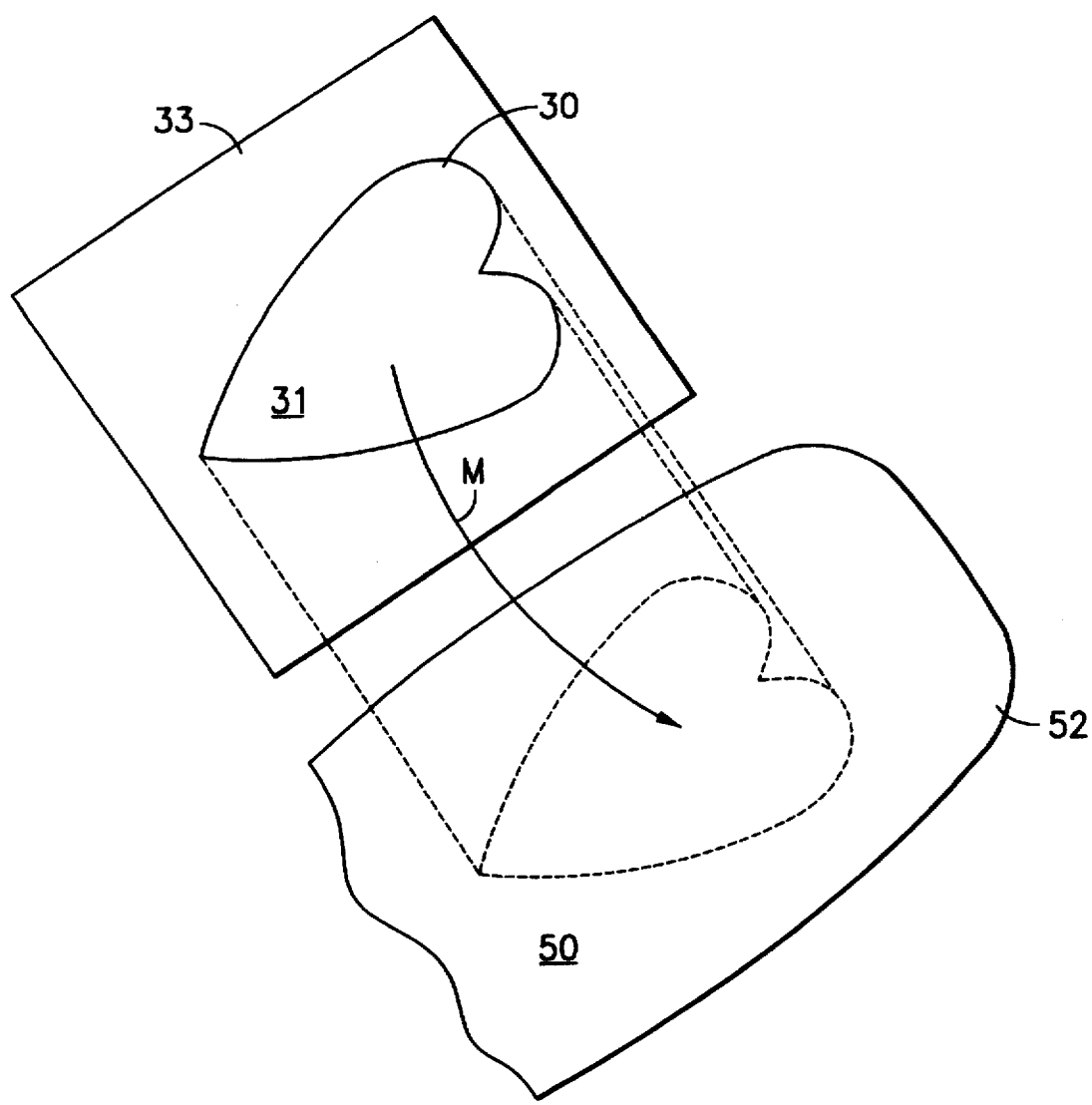
FIG. 5B is a perspective view of an appliqué being applied to a dental substrate in accordance with another embodiment of the invention.

FIG. 5B is a perspective view of an appliqué 30 being applied to a dental substrate 52 in accordance with another embodiment of the invention. The appliqué in this embodiment is secured as for example by a low tack adhesive to the transfer backing sheet 33. The appliqué on its front face 31 has an adhesive thereon (for ease of handling, the face 31 of the appliqué may originally have disposed thereover a protective peel-off sheet, to protect the adhesive on such face prior to application of the appliqué to the dental substrate).

As shown, the appliqué 30 is translated in the direction indicated by arrow M into facial contact of the appliqué face 31 with the surface 50 of the dental substrate 52. The appliqué may in such manner be manually pressed into place on the dental substrate, so that after such contacting and peeling away of the transfer backing sheet 33, the face 31 of the appliqué is bonded onto the surface 50 of the dental substrate.

Figure 6:
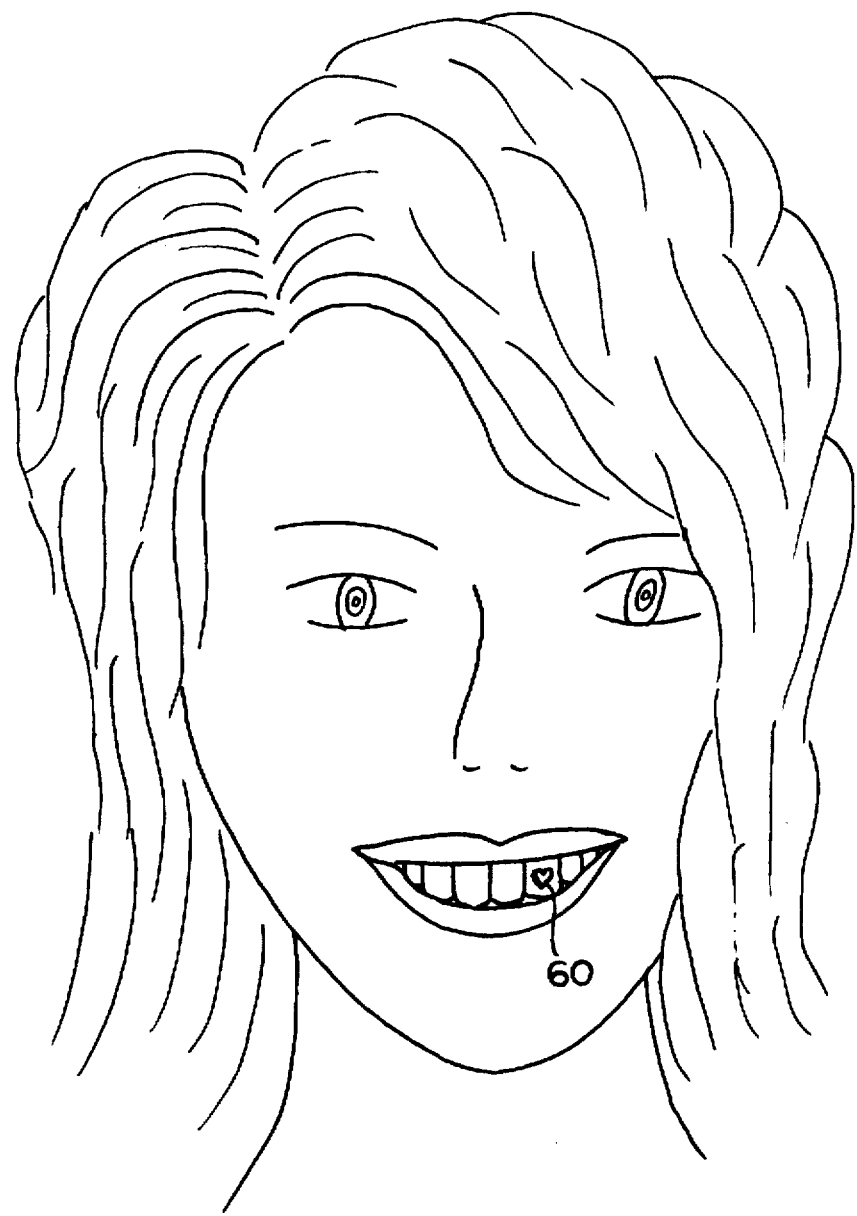
FIG. 6 is a front view of a wearer of the appliqué, subsequent to securement of the appliqué to the wearer's tooth.

FIG. 6 is a front view of a wearer of the appliqué 60, subsequent to securement of the appliqué to the wearer's tooth.

The wearer as shown has the appliqué 60 applied to the anterior surface of a lateral incisor which is one of the wearer's anterior teeth. Such frontal tooth positioning may be employed for purposes of maximum visibility. In other instances in which the appliqué is desired for identification purposes, the appliqué may be applied to a tooth surface in a less visible portion of the oral cavity, so that it is not visible during normal speech or during facial expressions exposing the teeth to view.

Figure 7:
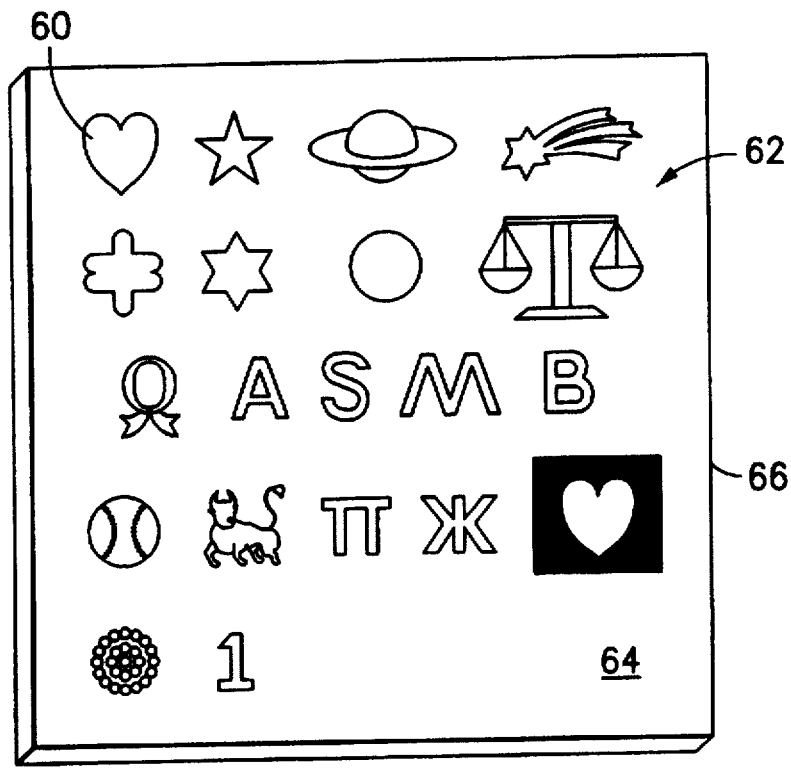
FIG. 7 is a perspective view of an array of appliqué articles, disposed on an adhesive backing contact sheet, for selective removal from the contact sheet and application to the surface of a dental substrate.

FIG. 7 is a perspective view of an array 62 of appliqué articles 60, disposed on the front surface 64 of an adhesive backing contact sheet 66, for selective removal of the appliqués from the contact sheet and application thereof to the surface of a dental substrate.

The contact sheet 66 on its front surface 64 may be coated with a coating of a release agent or other film or material to which the appliqué articles 60 are easily detatchably secured. Alternatively, the contact sheet 66 may itself be made of a suitable material, e.g., a low surface energy plastic, enabling ready detachment of the appliqué article 60 from surface 64.

By means of the array 62 presented on the contact sheet 66, a multiplicity of appliqué articles 60 is presented to the prospective wearer for selection. The appliqués as shown may be in the form of silhouettes, shaped cut outs, initials, geometrically regular shapes, astrological signs, letters, words, numeric or alphanumeric characters, and fanciful designs.

As mentioned, the appliqué design may be a cut out or "negative" design whereby a larger portion of the surface of the dental substrate is covered by the metal foil and a shape is cut out of the foil. The tooth or dental substrate surface is thereby exposed through the resulting border portion of the appliqué, to display on the dental substrate the shape of the cut out.

Figure 8:
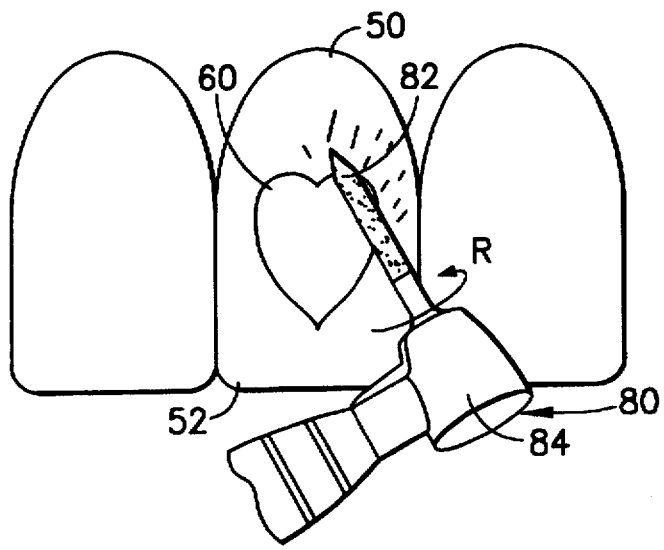
FIG. 8 is a perspective view showing the removal of the appliqué from a tooth surface by dental abrasion using a dental handpiece with a diamond-coated abrasion tip.

FIG. 8 is a perspective view showing the removal of an appliqué 60 from a tooth surface 50 by dental abrasion. As shown, the appliqué 60 is being abradingly removed from the surface 50 of tooth 52 by abrasive distal element 82 mounted, e.g., by chuck or other suitable coupling means, in the head 84 of dental handpiece 80. By such arrangement, the distal element 82 is rotated at sufficiently high speed, in the direction indicated by arrow R, so that when the abrasive distal element 82 is driven abradingly across the surface of the metal foil appliqué 60, the foil is readily stripped from the tooth surface 50.

Alternatively, the appliqué may be removed by use of a suitable safe and biocompatible solvent for the adhesive bonding the main body portion 30 of the appliqué to the tooth surface.

As a still further alternative, localized heat or cold can be briefly focused on the appliqué, so that differential thermal expansion effects cause the softening and/or delamination of the adhesive from the tooth surface, to thereby effect or enhance the removal of the appliqué from the tooth surface.

In some instances, particularly where the appliqué is desired to be temporarily worn on a tooth surface, and is secured in position by an appropriate temporary adhesive or bonding medium, it may be feasible and desirable to remove the appliqué from the tooth with an ultrasonic dental cleaning instrument.

A preferred method of removing the appliqué involves the use of a flame-shaped diamond or carbide burr or stone, followed by an enamel polishing procedure of coarse abrasives to fine abrasives to a diamond paste.

Figure 9:
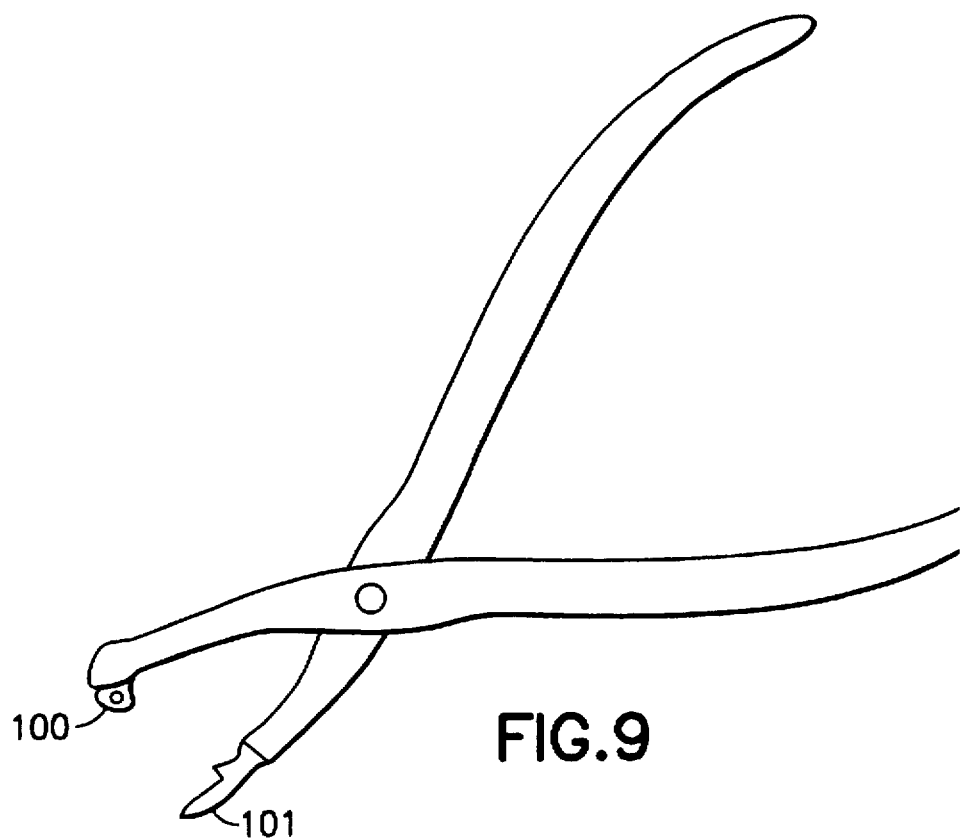
FIG. 9 is a perspective view of a pair of dental pliers used in an alternative method for removing the appliqué from the surface of a tooth.
Figure 10:
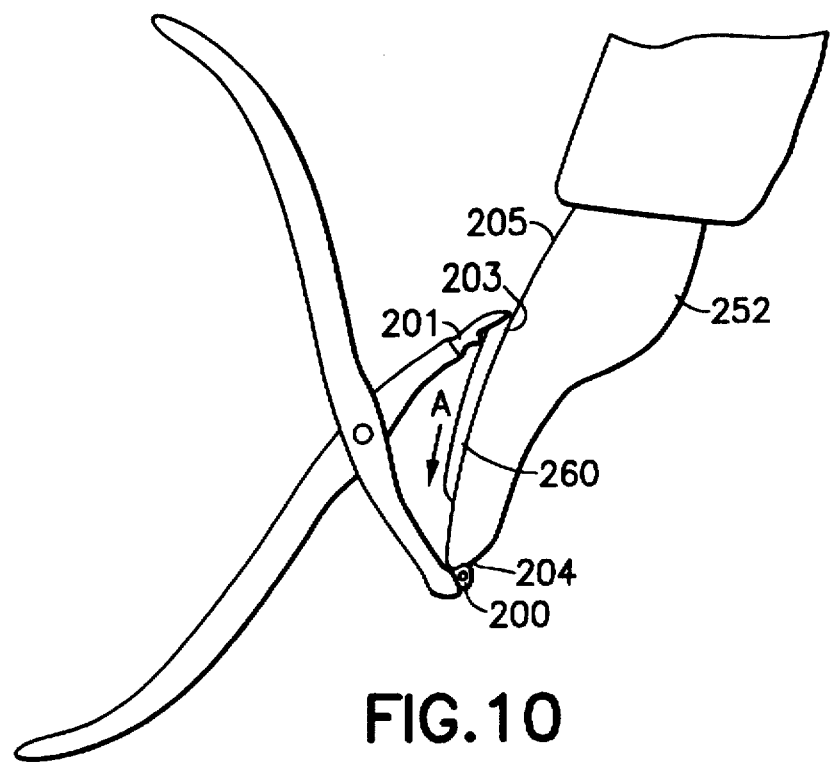
FIG. 10 is a side view of a pair of dental pliers in position to remove an appliqué from the surface of a tooth.

FIGS. 9 and 10 illustrate an alternative method for removing the appliqué from the dental substrate using a pair of dental pliers. In such an alternative method a pair of dental pliers of the general type shown in FIG. 9 is equipped with nylon padded tip 100 and carbide tip 101.

FIG. 10 shows such type of dental pliers in use, removing the appliqué from a tooth surface. Specifically, carbide tip 201 is hooked on gingival edge 203 of appliqué 260 which is attached to anterior surface 205 of tooth 252. The padded nylon tip 200 concurrently is positioned on incisal edge 204 of tooth 252. The pliers are activated and a lateral shearing force in the direction of arrow A is produced, to shearingly remove appliqué 260, wholly or partially, from the tooth 252.

Figure 11:
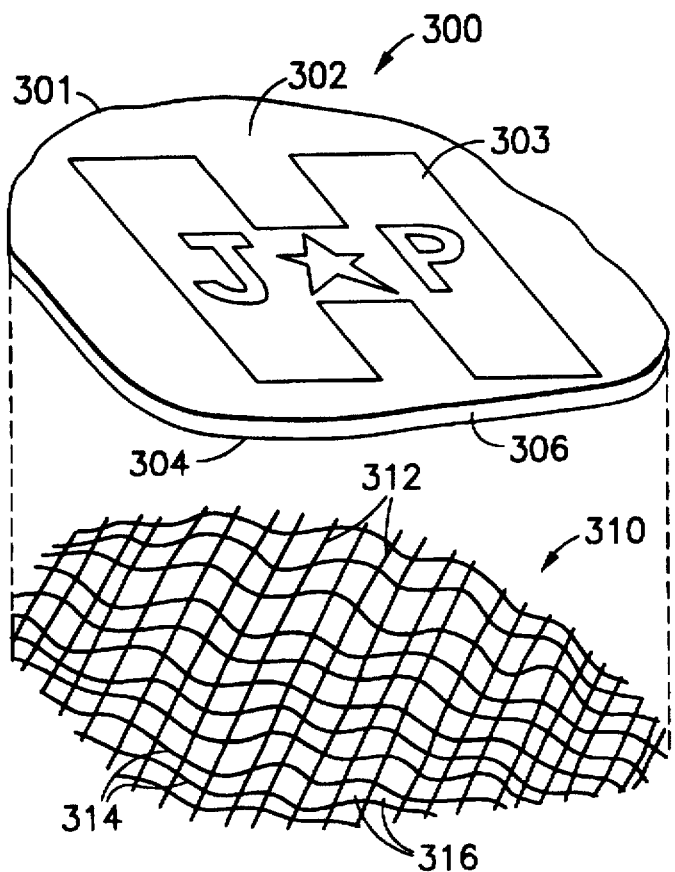
FIG. 11 is a perspective exploded view of an appliqué article according to another embodiment of the invention, comprising a metal foil body and a mesh backing member which is tack welded and then brazed to the metal foil body.

FIG. 11 is a perspective exploded view of an appliqué article 300 according to another embodiment of the invention, comprising a metal foil body 301 and a mesh backing member 310 which is tack welded and then brazed to the metal foil body.

The metal foil body 301 has a main top surface 302 and a main bottom surface 304 in the orientation shown. The main top surface 302 features a monogram design 303 thereon. The metal foil body has a side edge 306 defining a thickness between the main top surface 302 and the main bottom surface 304.

Disposed in matable relationship to the metal foil body 301 in the FIG. 11 embodiment is a mesh backing member 310, which comprises a criss-cross strand array including a first array of vertical strands 312 and a second array of horizontal strands 314, positioned at right angles with respect to one another to define a multiplicity of interstitial spaces 316 between adjacent parallel strands of each of the arrays. The mesh backing member 310 may as shown in the drawing have a contoured shape, being convex on the side engaging the metal foil body, and concave on the side engaging the dental substrate, over part or all of its surface areas. The metal foil body may be correspondingly contoured, with an outer surface of convex curvature, and an inner surface with a concave curvature, over part or all of its surface areas. The metal foil body may as also shown have a side edge 306 which is rolled or otherwise shaped, to better mate with the edge of the mesh backing member, i.e., so that the rolled edge of the metal foil body "frames" or wraps around the periphery of the mesh backing member to thereby form a conjoint mesh backing/foil structure when the backing and foil are secured to one another.

The mesh backing structure may be secured to the metal foil body of the appliqué in any suitable manner and with any suitable adhesive, bonding, coupling or securement medium. In preferred practice, the mesh backing member is tack welded to the foil body of the appliqué followed by brazing of the mesh backing member to the foil body, with the welding and brazing steps being carried out for sufficient time and at sufficient temperature to ensure the structural integrity of the resulting composite appliqué article in use. It will be understood that these welding and brazing steps may utilize standard fluxes or otherwise be carried out in a conventional manner as regards the nature of the bonding operation, to bond the mesh and foil members in the fabrication of the appliqué

Figure 12:
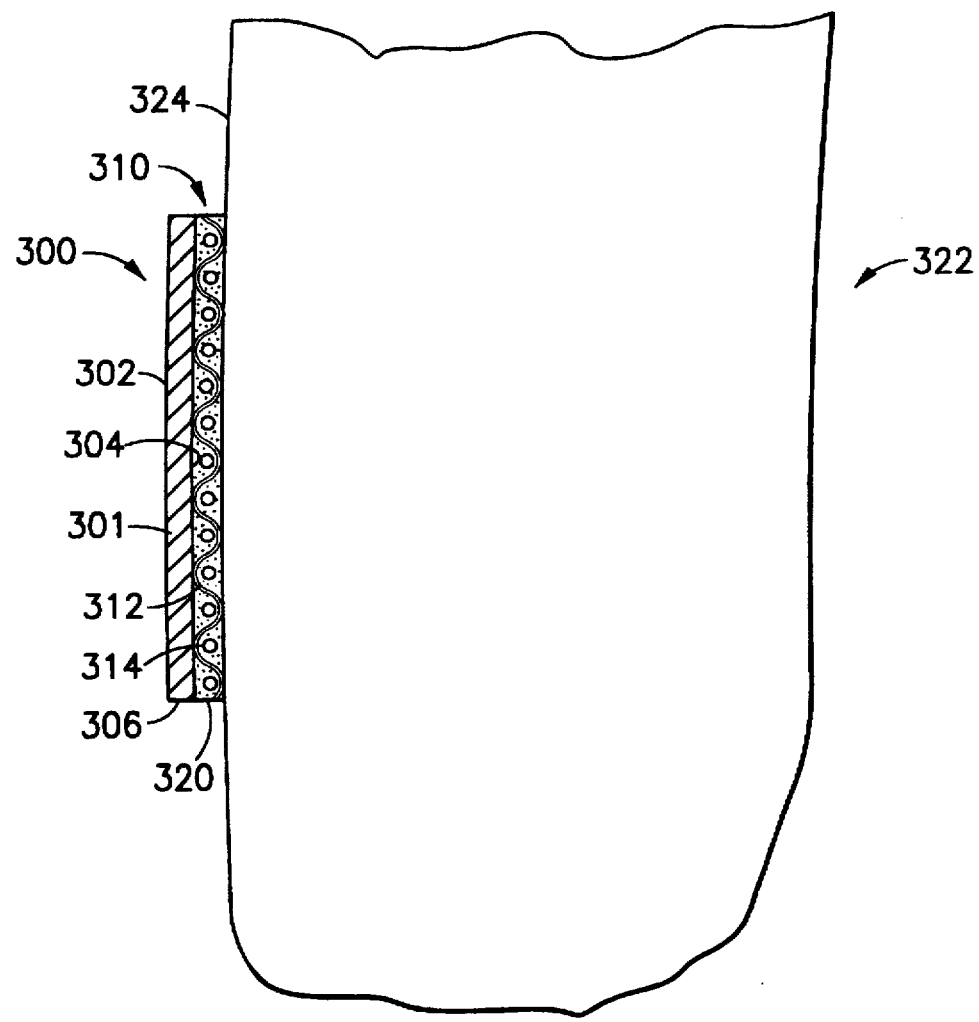
FIG. 12 is a cross-sectional side elevation view of the appliqué article of FIG. 11 shown as adhesively bonded to a dental substrate.

FIG. 12 is a cross-sectional side elevation view of the appliqué article 300 of FIG. 11 shown as adhesively bonded to a dental substrate 322. As illustrated, the appliqué article 300 as comprising the metal foil body 301, to the main bottom (rear) face 304 of which is brazed the mesh backing member 310, is adhesively bonded to the front surface 324 of the dental substrate 322 by adhesive 320. The adhesive 320 may comprise any suitable adhesive medium such as those illustratively discussed hereinabove for bonding the metal foil body directly to the dental substrate in the absence of an intermediate foraminous backing member.

By such mounting of the appliqué 300 on the front surface 324 of the dental substrate 322, the main top (front) surface 302 of the appliqué, bearing the decorative indicia thereon (not shown in FIG. 12; see FIG. 11), is presented to front view as a decorative artifact on the dental substrate surface 324.

In addition to the foraminous backing structure shown and herein described, the appliqué of the invention may comprise other non-foraminous or otherwise constructed backing or intermediate (between the foil and the dental substrate) structure, useful for securing the metal foil to the dental substrate.

Figure 13:
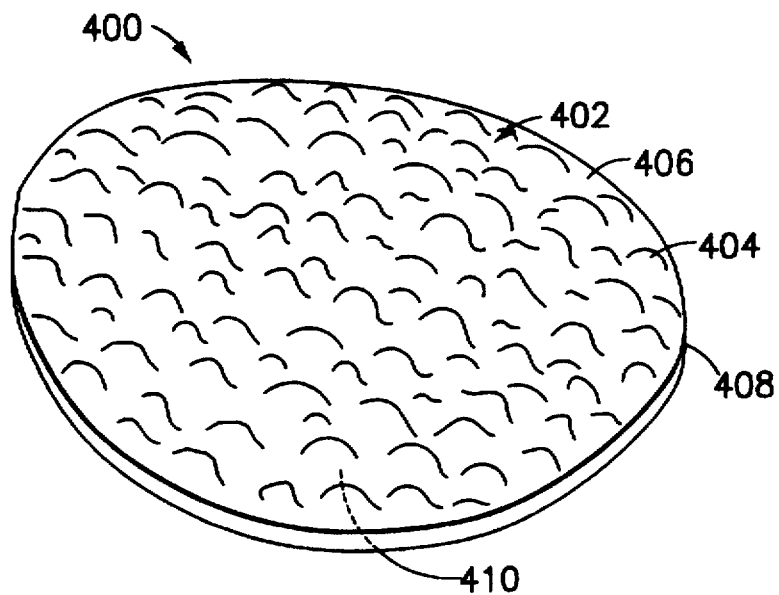
FIG. 13 is a perspective view of an appliqué article according to another embodiment of the invention, featuring a virtual mesh structure formed by discontinuously deposited metal on the rear surface of the metal foil of such appliqué article.

FIG. 13 is a perspective view of an appliqué article 400 according to another embodiment of the invention, featuring a virtual mesh structure 402 formed by discontinuously deposited metal 404 on the rear surface 406 of the metal foil 408 of such appliqué article. The front side 410 of the appliqué article may comprise a decorative motif, design, symbol, pictograph, or other applied layers thereon (e.g., of decorative enamel, other metals, clearcoat protective layer, etc.).

The discontinuously deposited metal 404 on the rear surface 406 of the appliqué metal foil 408 may be deposited thereon by sputtering, chemical vapor deposition, physical vapor deposition, electroless or electrolytic deposition, metal spray, solution evaporation, or any other suitable technique, to thereby apply a same or different metal (relative to the metal constituent(s) of the foil). By such deposition, a discontinuous deposit of metal is provided on the rear surface of the appliqué metal foil (the surface which when the appliqué metal foil is secured to the tooth, will be facing the tooth surface) to form a textured surface. Such surface will therefore have surface asperities thereon formed by the deposited metal, providing involutions and/or discontinuities in the applied metal which enhance the bondability of the appliqué metal foil to the dental substrate. In such manner, a "virtual mesh" structure is provided by the discontinuous metal applied to the back of the metal foil, by means of which the appliqué is readily adhesively bondable to the dental substrate. The discontinuous metal applied to the back of the metal foil of the appliqué may be discontinuously formed by masking of the metal foil rear surface, patterning the rear surface using suitable mask and/or photoresist reagents, or otherwise utilizing deposition techniques of known character to form discrete or particulate islands of the applied metal on the rear surface of the appliqué.

The features and advantages of the invention are more fully illustrated by the following, non-limiting examples.

EXAMPLE I

A tooth (left lateral incisor) is prepared by etching its anterior surface with Etchant-Light Green (Reliance Orthodontic Products, Itasca, Ill.). A piece of transparent tape (Scotch™ Tape, 3M Company, St. Paul, Minn.) is attached to the polished side of a heart shaped gold foil appliqué having a polished side and a microetched side. Transbond Light Cure Orthodontic Adhesive system (3M Unitek Corporation, Monrovia, Calif.) is applied to the microetched side of the gold foil appliqué.

The appliqué with adhesive applied thereon is carried to the anterior surface of the prepared left lateral incisor via a tweezer grasping the edge of the transparent tape. The appliqué is initially placed on the anterior surface of the tooth with the adhesive side down. The tape then is peeled off of the appliqué. A blunt instrument is used to finally position the gold foil appliqué on the anterior surface of the tooth. A dental explorer is used to clean the margins of the appliqué. High intensity light is applied to the appliqué to cure the adhesive, thereby fixing the appliqué in place on the tooth.

EXAMPLE II

A tooth (left lateral incisor) is prepared as in Example I. An appliqué article of the type shown in FIGS. 11 and 12 is employed. The appliqué comprises a main foil body having a thickness of 0.10 inch, formed of a gold dental alloy, joined to a mesh backing member formed of stainless steel wire having strands with a diameter of 0.004 inch. The mesh backing member has a mesh size of 80, with 0.007 inch spacing between the parallel wires in each of the vertical and horizontal strand arrays of the mesh. The mesh is tack welded to the metal foil and then brazed thereto. The resulting foil/mesh composite has a thickness on the order of 0.013–0.014 inch. The main top surface of the foil body (opposite the mesh side of the foil body) is polished to provide an aesthetic visual appearance.

A piece of transparent tape (Scotch™ Tape, 3M Company, St. Paul, Minn.) is attached to the polished side of the gold foil appliqué. Adhesive system (3M Unitek Corporation, Monrovia, Calif.) is applied to the mesh side of the gold foil appliqué to thoroughly coat the mesh and penetrate the interstices thereof.

The appliqué with adhesive applied on the mesh side thereof is carried to the anterior surface of the prepared left lateral incisor via a tweezer grasping the edge of the transparent tape. The appliqué is initially placed on the anterior surface of the tooth with the adhesive side down. The tape then is peeled off of the appliqué. A blunt instrument is used to finally position the gold foil appliqué on the anterior surface of the tooth, with the mesh in good contact with the tooth surface, as well as the surface of the foil to which it is brazed. A dental explorer is used to clean the margins of the appliqué. High intensity light is applied to the appliqué to cure the adhesive, thereby fixing the appliqué in place on the tooth.

While the invention has been described herein with respect to various illustrative embodiments, features, and aspects, it will be appreciated that numerous other variations, modifications, and other embodiments are contemplated within the broad scope of the invention as disclosed and claimed herein, and the invention therefore is to be correspondingly broadly construed to encompass all such other variations, modifications, and other embodiments within its spirit and scope.

What is claimed is:

1. A metal foil appliqué for adhesive bonding to a dental substrate, comprising a metal foil body having main top and bottom faces of a predetermined shape and a side edge, said main bottom face having a foraminous backing structure secured thereto, wherein the main bottom face is adapted for affixation to the dental substrate over at least a major portion of its facial area by securement of said foraminous backing structure to said dental substrate for spacing said appliqué from said substrate, said foil body side edge shaped to frame the periphery of said foraminous backing structure.

2. A metal foil appliqué according to claim 1, wherein the foraminous backing structure is brazed to the main bottom surface of the metal foil body.

3. A metal foil appliqué according to claim 1, wherein the metal foil body is adapted for bonding to the dental substrate with an adhesive medium on a major portion of its facial area having the foraminous backing structure secured thereto.

4. A metal foil appliqué according to claim 1, wherein the metal foil body is adapted for bonding to the dental substrate by said foraminous backing structure bearing an adhesive medium thereon.

5. A metal foil appliqué according to claim 1, wherein the metal foil body has a shaped edge surface.

6. A metal foil appliqué according to claim 1, wherein the metal foil body has a maximum facial dimension not exceeding 1 centimeter.

7. A metal foil appliqué according to claim 1, wherein the metal foil body comprises a metal selected from the group consisting of copper, brass, bronze, platinum, palladium, gold, silver, iridium, rheuthenium, chromium, stainless steel, aluminum, titanium, and alloys, mixtures, and composites thereof.

8. A metal foil appliqué according to claim 1, wherein the metal foil body comprises a high noble metal.

9. A metal foil appliqué according to claim 1, wherein the metal foil body comprises a gold foil.

10. A metal foil appliqué according to claim 1, wherein the thickness of said metal foil body is from about 0.02 millimeter to about 0.5 millimeter.

11. A metal foil appliqué according to claim 1, wherein the thickness of said metal foil body is from about 0.04 millimeter to about 0.25 millimeter.

12. A metal foil appliqué according to claim 1, wherein the maximum facial area dimension does not exceed 0.75 square centimeter.

13. A metal foil appliqué according to claim 1, wherein the maximum facial area dimension does not exceed 0.6 square centimeter.

14. A metal foil appliqué according to claim 1, wherein the metal foil body presents an ornamentation selected from the group consisting of silhouettes, initials, geometrically regular shapes, cut outs, words, alphanumerics, numerics, and fanciful designs.

15. A dental article according to claim 1, further including said dental substrate, wherein the dental substrate comprises an artificial denture article.

16. A dental article according to claim 1, including an adhesive for securing said metal foil appliqué to the dental substrate, selected from the group consisting of light curing adhesives and self-curing adhesives.

17. A method of ornamenting a dental substrate, comprising:

providing an ornamental metal foil appliqué, comprising a metal foil body with main top and bottom surfaces, a foraminous backing structure secured to the main bottom surface and said foil body having a side edge shaped to frame the periphery of said foraminous backing structure;

bonding the foraminous backing structure of the metal foil appliqué to the dental substrate so that the ornamental metal foil appliqué is spaced from the dental substrate.

18. A method according to claim 17, further comprising imparting to the metal foil, prior to its bonding to the dental substrate, a predetermined shape with a maximum facial area dimension not exceeding 1 square centimeter.

19. A method according to claim 17, further comprising bonding the main bottom surface of the metal foil through the foraminous backing structure to the dental substrate by an adhesive medium.

20. A method according to claim 17, wherein the foraminous backing structure comprises a mesh backing member.

21. A method according to claim 20, comprising securing the foraminous backing structure to the metal foil by tack welding followed by brazing.

22. A method according to claim 17, wherein the ornamentation is reversible, with the foraminous backing of the metal appliqué when bonded to the dental substrate allowing ready removal of the foil appliqué from the dental substrate by application of a shearing force applied at said foraminous backing structure between said appliqué bottom face and said dental substrate.

23. A method of temporarily ornamenting a dental substrate, comprising:

providing an ornamental metal foil appliqué, comprising a metal foil body with main top and bottom surfaces, a foraminous backing structure secured to the main bottom surface and said foil body having a side edge shaped to frame the periphery of said foraminous backing structure;

bonding the foraminous backing of the metal foil appliqué to the dental substrate so that the ornamental metal foil appliqué is spaced from the dental substrate and is oriented in a selected display position on the dental substrate presenting the main top surface of the metal foil appliqué to view;

displaying the ornamental metal foil appliqué on the dental substrate; and after a period of time, removing the ornamental metal foil appliqué from the dental substrate.

24. A method according to claim 23, wherein the removal of the ornamental metal foil appliqué from the dental substrate comprises abradingly removing the metal foil appliqué from the dental substrate.

25. A method according to claim 23, wherein the removal of the ornamental metal foil appliqué from the dental substrate comprises shearingly removing the metal foil appliqué from the dental substrate.

26. A method according to claim 23, wherein the removal of the ornamental metal foil appliqué from the dental substrate comprises removing the metal foil appliqué from the dental substrate with an abrasive tool.

27. A method according to claim 23, wherein the removal of the ornamental metal foil appliqué from the dental substrate comprises removing the metal foil appliqué from the dental substrate with a pliers including a first jaw member engaging the dental substrate, and a second jaw member engaging the ornamental metal foil appliqué, so that closing engagement of the first and second jaw members effects removal of the ornamental metal foil appliqué from the dental substrate, wherein the spacing between the appliqué and the dental substrate provided by the foraminous backing provides an enhanced purchase for the second jaw member.

28. The method of temporarily ornamenting a dental substrate according to claim 27, wherein:

the first jaw is configured as a padded concave hook adapted to mate with a bite edge of the dental substrate, and said second jaw is unpadded and adapted to engage the edge and bottom face of said ornamental appliqué and to engage the foraminous backing.

* * * * *